US008065095B2

(12) United States Patent
Rekenthaler et al.

(10) Patent No.: US 8,065,095 B2
(45) Date of Patent: Nov. 22, 2011

(54) SYSTEMS FOR TERRESTRIAL TARGET DETECTION AND CHARACTERIZATION USING A DISPERSED FOURIER TRANSFORM SPECTROMETER

(76) Inventors: Douglas A. Rekenthaler, Sioux City, IA (US); Arsen R. Hajian, Waterloo (CA); Douglas G. Currie, Silver Spring, MD (US); Andrei V. Smirnov, Boulder, CO (US)

( * ) Notice: Subject to any disclaimer, the term of this patent is extended or adjusted under 35 U.S.C. 154(b) by 464 days.

(21) Appl. No.: 12/255,854

(22) Filed: Oct. 22, 2008

(65) Prior Publication Data
US 2010/0274501 A1 Oct. 28, 2010

Related U.S. Application Data

(60) Provisional application No. 60/982,896, filed on Oct. 26, 2007.

(51) Int. Cl.
*G06F 19/00* (2011.01)

(52) U.S. Cl. ............................................ 702/28
(58) Field of Classification Search .................. 702/28, 702/182–185, 188
See application file for complete search history.

(56) References Cited

U.S. PATENT DOCUMENTS 7,206,073 B2  4/2007 Hajian et al.
7,583,710 B2 * 9/2009 Dantus et al. .................. 372/25

* cited by examiner

*Primary Examiner* — Edward Raymond
(74) *Attorney, Agent, or Firm* — Dickstein Shapiro LLP

(57) ABSTRACT

A precision molecular and motion sensor utilizing a Dispersed Fourier Transform Spectrometer to remotely sense targets. Remote sensing is conducted at various ranges, against various ambient backgrounds, to detect, classify, identify, characterize, and discriminate targets. A Dispersed Fourier Transform Spectrometer is expanded by modification and augmentation of existing optical, mechanical, and software components to enable basic terrestrial use while providing specific optimization for various applications which are designed with emphasis on the sensitivity of the Dispersed Fourier Transform Spectrometer.

21 Claims, 12 Drawing Sheets

Infrasonic Sensor Configuration

US 8,065,095 B2

SYSTEMS FOR TERRESTRIAL TARGET DETECTION AND CHARACTERIZATION USING A DISPERSED FOURIER TRANSFORM SPECTROMETER

This application claims priority to U.S. Provisional Application No. 60/982,896, filed on Oct. 26, 2007, which is hereby incorporated by reference in its entirety.

FIELD OF THE INVENTION

Embodiments of the invention relate to systems that utilize a Dispersed Fourier Transform Spectrometer. More specifically, embodiments of the invention relate to systems that remotely sense and exploit targets which are within various line-of-sight ranges, and set before various complex backgrounds, to enable detection, identification, classification, characterization, and discrimination.

BACKGROUND OF THE INVENTION

The Dispersed Fourier Transform Spectrometer (DFTS) is a further modernization of the 1883 invention by Dr. Albert Michelson, who laid the theoretical basis for the Fourier Transform Spectrometer (FTS). The DFTS, as outlined in U.S. Pat. No. 7,206,073, which is hereby incorporated by reference in its entirety, consists of an FTS with a grating spectrometer and a metrology sub-system that can discern sub-nanometer vibrations and displacements, as well as discriminate and identify molecular species.

The DFTS was designed to investigate and characterize extra-solar stellar masses and motions at cosmic distances; it possesses the requisite high level of sensitivity to accomplish such tasks. However, the DFTS has not been applied to the problem of remotely sensing targets within the terrestrial domain. It is desirable to provide both systems and methods of implementing such systems, which capitalize on the capability of the DFTS to both: (1) detect differential motions and vibrations by measuring the variation in fringe shifts present with different spectral bands, and (2) differentiate between molecular species by using combinations of different spectral bands.

SUMMARY OF THE INVENTION

The DFTS, as disclosed in U.S. Pat. No. 7,206,073, is optimized for astronomy- and astrometric-based applications which require measurement of stellar radiation, spectral compositions, and stellar motions. These measurements require the use of astronomical telescopes; particularly the large mirrors of astronomical telescopes which act as photon collection sources. The hardware and software apparatus of embodiments of the present invention use a variant of the DFTS as one element in a more complex system configuration. Specifically, embodiments of the invention incorporate appropriate stabilization and tracking mechanisms to allow the apparatus the capability of extremely precise airborne, land based, or space-based remote sensing for a variety of terrestrial applications.

Embodiments of the invention incorporate an optical collector and a DFTS-based instrument package augmented with: (1) a source of active or passive illumination; (2) a photon collection apparatus, which may comprise a telescope, rifle scope, mirror, fiber optic bundle, a combination of the aforementioned, or other photon collection apparatus known by persons having ordinary skill in the art, (3) a fiber optic link—point, line, or array arrangement, tailored to the type of target being sensed—between the photon collector and the DFTS; (4) DFTS optics and electronics, suitably tailored for the specific application; (5) a tuned diffraction grating, tailored for the specific digital record of the spectral target signatures necessary for a specific application; (6) an analog-to-digital converter; (7) an appropriate recording apparatus; (8) a stored digital record of the spectral target signatures for a specific application; (9) a stored digital record of the anticipated, application-specific, ambient background noise and clutter; (10) where possible, a stored, nonlinear attractor software model of the anticipated signal and noise associated with a specific application; (11) a data processing device to correlate and display the output; and (12) the appropriate pointing and tracking mechanisms.

Additional features and advantages of the embodiments will be set forth in the description which follows and will be apparent from the description or may be learned by practice of the invention.

DETAILED DESCRIPTION OF THE INVENTION

In the following detailed description, reference is made to the accompanying drawings, which form a part hereof and show by way of illustration specific embodiments in which the invention may be practiced. These embodiments are described in sufficient detail to enable those skilled in the art to practice them, and it is to be understood that other embodiments may be utilized, and that structural, logical, mechanical, optical, and electrical changes may be made.

Definitions

The term "Sensor" as used herein refers collectively to the hardware and software apparatus, specified in the embodiments listed herein, which may be used to remotely sense targets within various line-of-sight ranges, and set before various complex backgrounds, to enable detection, identification, classification, characterization, and discrimination.

The term "Dispersed Fourier Transform Spectrometer" refers to the invention described in U.S. Pat. No. 7,206,073.

The term "target" refers to an object of interest capable of being sensed by the Sensor, and may include, but is not limited to, solids, aerosols, liquid surfaces, particles, or gases.

The term "background" refers to the ambient, natural, or anthropomorphic surroundings against which a target may be viewed. Elements and features of the background may enhance, hinder, or fail to meaningfully impact the performance of the Sensor.

The term "detect" refers to the ability to find a target of interest in a field of view.

The term "classify" refers to the ability to acquire sufficient information about a target to determine the general class within which the target may be included.

The term "characterize" refers to the ability to specify certain features of a target, including, but not limited to, color, brightness, chemical composition, surface treatment, toxicity, state of motion, size, mass, attitude, and relative or absolute position within a field of view.

The term "discriminate" refers to the ability to isolate a target within the field of view from the background.

The term "attitude" refers to the relative orientation, or pose, of an object in the field of view.

Figure 1:
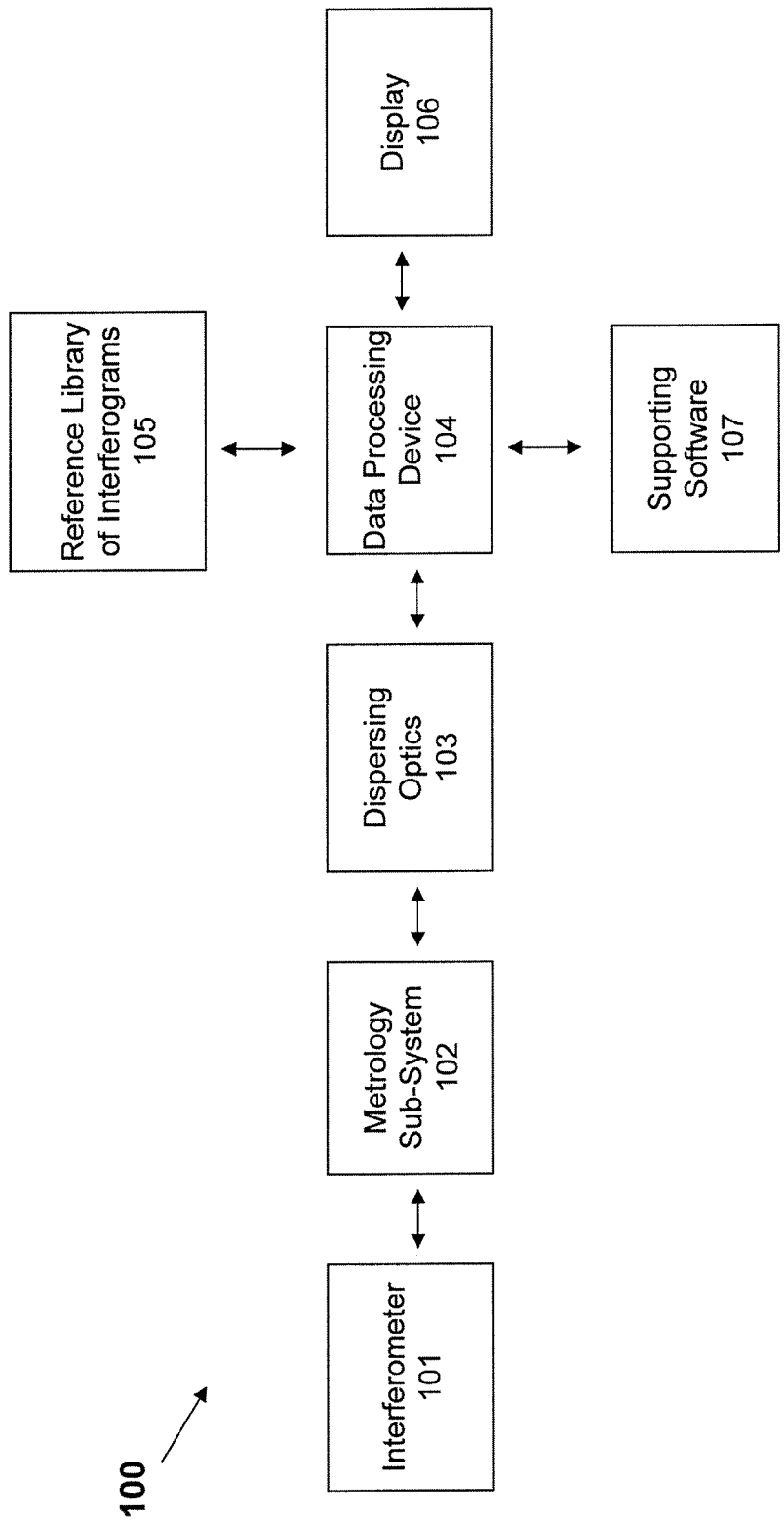
FIG. 1 is a block diagram of the principal components of a DFTS according to related art.

Referring now to FIG. 1, a conventional DFTS 100 comprises an interferometer 101, a metrology sub-system 102, diffraction grating or other dispersing optics element 103, data processing device 104, stored library of reference interferograms 105, display 106, and supporting software 107. The embodiments discussed herein will use a similar DFTS as one component of the novel Sensor disclosed herein. A representative Sensor is pictured in FIG. 3.

Figure 2:
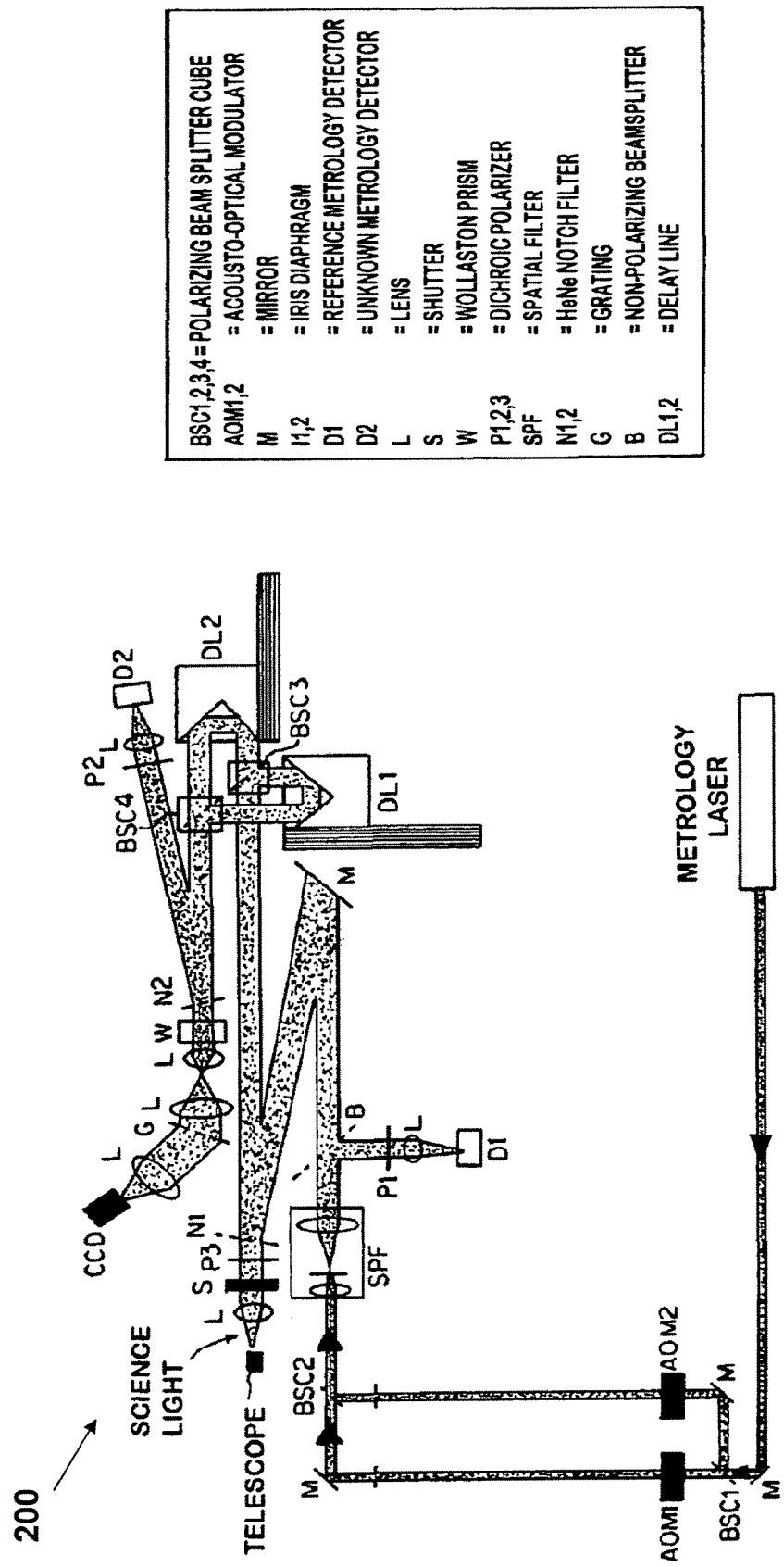
FIG. 2 is a schematic diagram of a DFTS according to related art.

FIG. 2 illustrates more details of a prior art DFTS interferometer 200. Two light beams enter the DFTS interferometer, one from the source to be measured and the other from the laser metrology system. Light from the metrology laser is split into two beams with orthogonal polarizations at BSC1. The two beams are frequency shifted (AOM1, AOM2), recombined BSC2, and spatially filtered and expanded SPF to the same size as the science light beam. Part of the recombined beam is split from the main beam B, both orthogonal polarizations are mixed at polarizer P1 and focused onto reference detector D1. Light from the source to be measured enters the spectrometer through polarizer P3. Polarized science light is combined with metrology light at notch filter N1. The combined beam is split into two by polarizing beamsplitter BSC3. Each beam propagates through DL1 or DL2. The beams are recombined at polarizing beamsplitter BSC4. The metrology light is separated from the combined light using notch filter N2, the orthogonal polarizations are mixed with polarizer P2 and sent to the metrology detector D2. The intensity measured at D2 is compared with that measured at D1 to generate the metrology signal. At this point, a conventional FTS would focus the light transmitted through N2 to a detector. Instead, with the DFTS interferometer, the light is sent to a dispersing spectrometer as shown. The two polarizations are separated with a Wollaston prism W, dispersed with a transmission grating G, and are each focused onto a row of pixels on charge-coupled device CCD or other imager.

Figure 3:
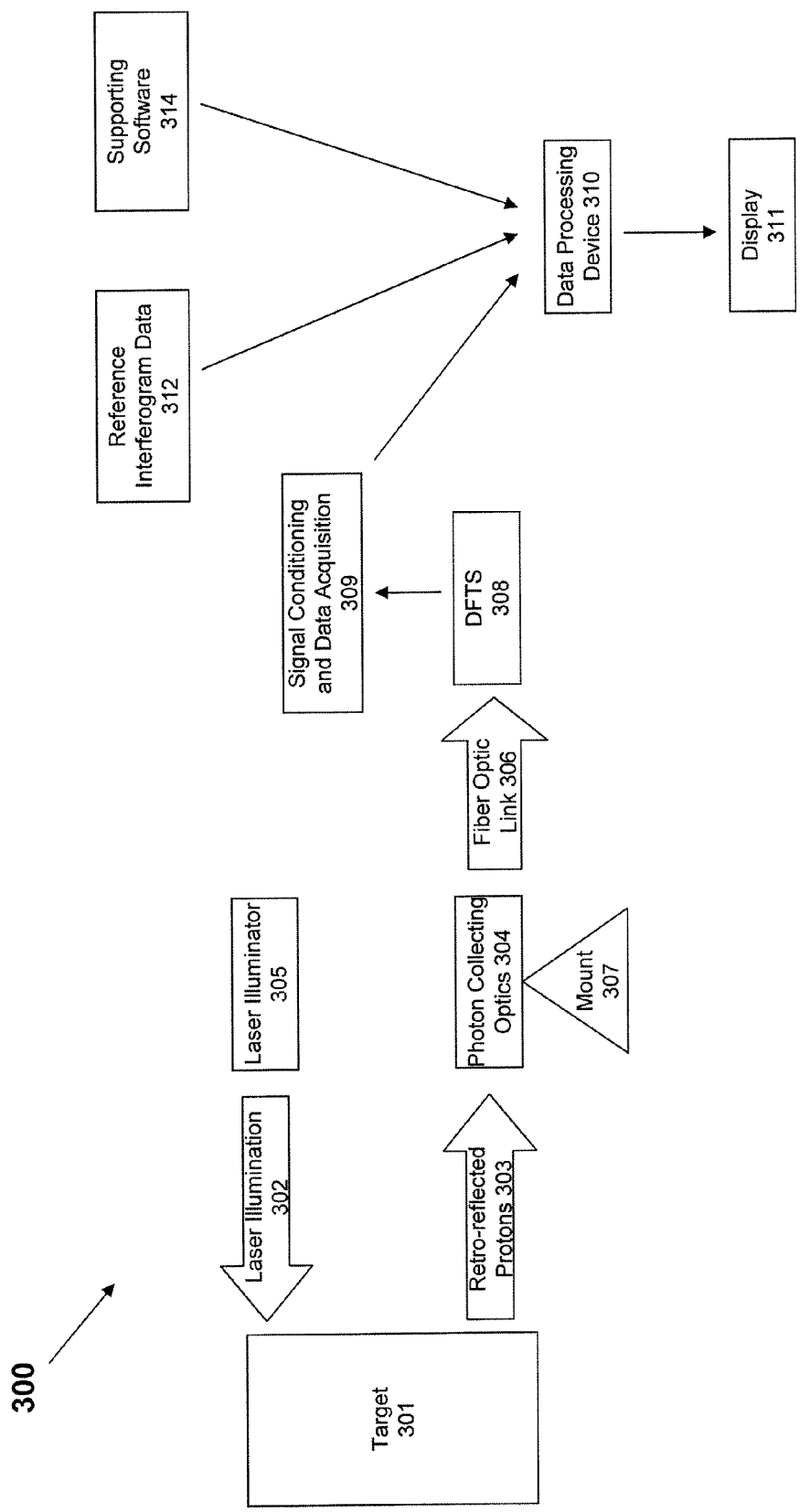
FIG. 3 depicts a system according to an embodiment described herein.

Referring now to FIG. 3, a Sensor 300 configured in accordance with an embodiment of the invention is shown and now described. In this embodiment, photon collecting optics 304 comprise either a lens or mirror, or a plurality of lenses or mirrors, and must be mounted on a stable body 307 to enable the control necessary for accurate azimuth and elevation inputs. Photon collection optics 304 are used to acquire incoming photons 303, which emanate from the target 301. These emanated photons may result from retro-reflections of ambient sunlight, or they may be retro-reflected from a source of anthropomorphic illumination, including, but not limited to, a spotlight or laser 305 (which emits laser illumination 302). Photon acquisition will be discussed in greater detail later in the application. The reflected or refracted photons 303 are passed through a fiber optic link 306 to the DFTS 308 where the functions of the DFTS are performed.

The digital output of the DFTS 308, in the form of interferogram data, flows to a signal conditioning and data acquisition circuit/device 309 and then to a data processing device 310 where the data interferogram is recorded, processed, correlated, and compared with reference model interferogram data 312. The reference model interferogram data 312 is resident within a digital library within the aforementioned data processing device memory, using supporting signal processing software 314. The resulting data and graphics are provided to the user on a display 311.

Photons are acquired by the Sensor 300 from either a passive, actively excited, or self-illuminating target. An example of a passive target could be a dispersed target, such as gaseous or particulate emissions from a smokestack that are illuminated by solar radiation. In this situation, the emissions may be viewed as retro-reflections, with the Sensor 300 on the solar side of the emissions, or the Sensor 300 may view the target 301 on the back side of the emissions. An example of an actively excited target 301 would be the stimulation of target phosphorescence or fluorescence by illuminating the target with a laser 305 having the appropriate wavelength. One example of a self-illuminating target would be a target having a surface brightness because of internal thermal heat. These examples serve only to illustrate that while illumination of a target may be required in certain instances, the Sensor 300 will function in many cases using ambient solar radiation.

Photon acquisition will be greatly enhanced when taking place within solar spectrums of the earth, which are considered dark regions, or dark spectral bands. The low background radiation in these regions results in both low background noise and clutter which will enable a Sensor being employed in these regions to have a much higher probability of successfully discriminating a target. Illumination of a target with a radiating illuminator, including, but not limited to, a laser or other source of light, which is operating at one or more of these dark spectral bands provides a means to enhance the signal-to-noise ratio. A high signal-to-noise ratio makes target acquisition more timely, minimizes necessary photon acquisition time, allows the Sensor to operate at greater altitude or range, and increases the probability of target detection while minimizing false alarms.

As presented previously, the Sensor 300 requires collecting optics 304. Types of collecting optics which can be used with the Sensor 300 include, but are not limited to, reflecting optics, refracting optics, fiber optic links, or bundles of fiber optics. Selection of an appropriate optic for the task will require consideration of, among other things, speed, altitude, motion, range, and brightness within the spectral bands of interest of the target, ability to access the target, background brightness, computational power of the data processing unit, sensitivity of the receiver, width of the spectral bands of interest, and Sensor platform speed. Each individual remote sensing scenario will require analysis to determine the optimal configuration necessary for the collecting optics.

Once collected by the optics, the photons in each spectral band pass through the DFTS 308. Optical path changes cause fringe shifts to appear at the output. Preliminary laboratory work will be necessary to determine either (1) the spectral bands which a particular target will respond to, possibly from incipient radiation from a laser, or (2) those spectral bands in which the target will be luminous from self-radiation, or (3) those spectral bands at which a target will reflect ambient sunlight. The results of this preliminary laboratory work will be stored in a signature library within the Sensor's data processing device 310.

Figure 4:
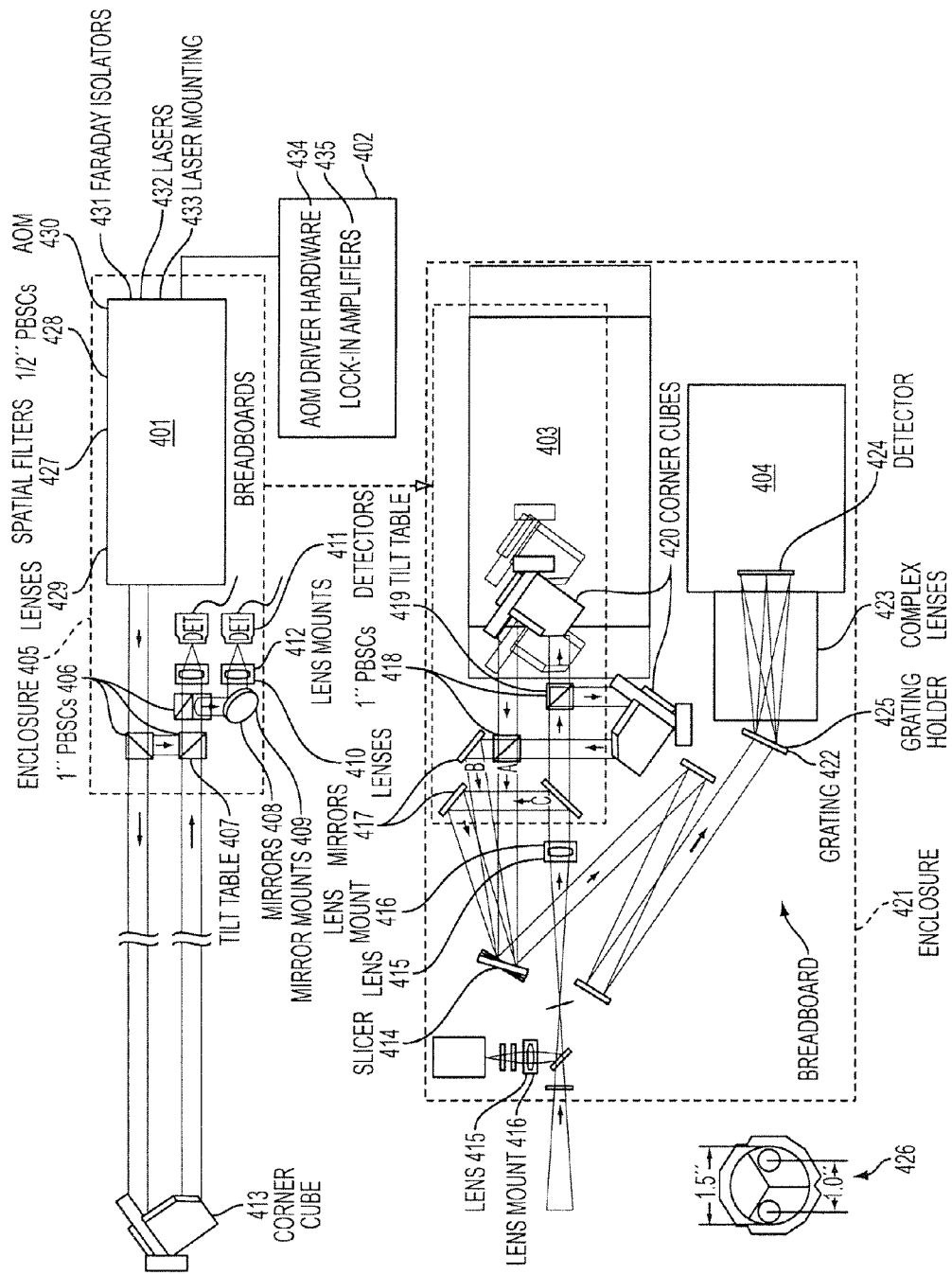
FIG. 4 depicts a more detailed view of an example DFTS configuration with an augmenting Metrology sub-system to increase its accuracy.

FIG. 4 depicts a detailed arrangement of the components of a typical DFTS and a typical metrology sub-system, in a representative configuration, with details of the relative spacing and arrangement of the component parts. FIG. 4 shows the DFTS spectrometric assembly described above, and a Metrology sub-system (described below). In practice, the DFTS assembly is mounted directly above the Metrology sub-system in a compact package, which as currently designed is a half-cubic foot in size, and a weight of less than 20 kilograms. However, designs for the entire DFTS Sensor, including the Metrology sub-system, may be configured in a few cubic centimeters or smaller. As depicted in FIG. 4, the DFTS Sensor is a WOMP (without moving parts) device, and the components are COTS (commercial, off-the-shelf), commonly available optical, electronic parts.

As shown in FIG. 4, optical sub-assembly 401 is enclosed in an enclosure 405 and resides on breadboards comprising one inch Polarizing Beam-Splitter Cubes ("PBSCs") 406, lenses 429, spatial filters 427, Acoustic-Optical Modulator ("AOM") 430, half inch PBSCs 428, Faraday isolators 431, lasers 432 (with laser mounting 433), detectors 411, lenses 410 on lens mounts 412, mirrors 408 on mirror mounts 409 and a tilt table 407. A corner cube 413 is used to receive and reflect photons from sub-assembly 401. Sub-assembly 401 is connected to acoustic-optical modulator sub-assembly 402, which contains AOM drivers 434 and lock-in amplifiers 435. Enclosure 421 houses assembly 403 and assembly 404 as well as slicer 414, lenses 415 (on mounts 416), mirrors 417, one inch PBSCs 418, tilt table 419, corner cubes 420, grating 422 (and grating holder 425), complex lenses 423 and detector 424. It should be appreciated that FIG. 4 is one example of the components that could be used in a system in accordance with an embodiment of the invention; accordingly, the claimed invention should not be limited to the example components illustrated in FIG. 4. An end-on view of an example corner-cube retro-reflector 426 is depicted, showing incoming photon beam and outgoing, reflected, photon beam from two segments of the retro-reflector (the entire corner-cube retro-reflector is not used).

When the Sensor is engaged in remotely sensing a target, slight target motions will produce fringe shifts that differ for each individual spectral band. The careful selection of spectral bands that correlate to the unique signatures of specific targets of interest will allow particular targets to be discriminated. Some applications may require the use of multiple illuminators arrayed in a bi-static manner. Other applications may require the use of multiple Sensors functioning as stereo receivers. Motion of the target, or motion of the Sensor, including use of a jitter or small motion mode may also be used to enhance the Sensor's performance. Additionally, there are applications where sensing of the target may be accomplished indirectly by sensing the target's shadow against the background rather than the target itself, or by illuminating the background and not the target. In these specific circumstances the application will dictate the arrangement of the illuminator, Sensor, and the target discrimination process.

It is important to recognize that targets may not have a tell-tale signature at one single discrete spectral band. Most targets will require sensing their response in several different spectral bands, with the characteristics of each target—in response to each spectral band—being stored in the spectral band data library on the Sensor's data processing device. For example, the Sensor's data processing device 310 (FIG. 3) would store different intensities and breadths for spectral bands used to identify foliage as opposed to those used to identify camouflage netting.

The Sensor will be optimized for use in one of three example embodiments, comprising: (1) spectrometric discrimination of a target's molecular composition; (2) measurement of relative range and motion, including vibration; or (3) a combination of embodiments (1) and (2). The use of several examples best illustrates the Sensor's design and functionality for these concepts. These examples are illustrative, and are not to be deemed as limiting.

Examples for the embodiment using spectrometric discrimination of a target's molecular composition are presented first.

Figure 5:
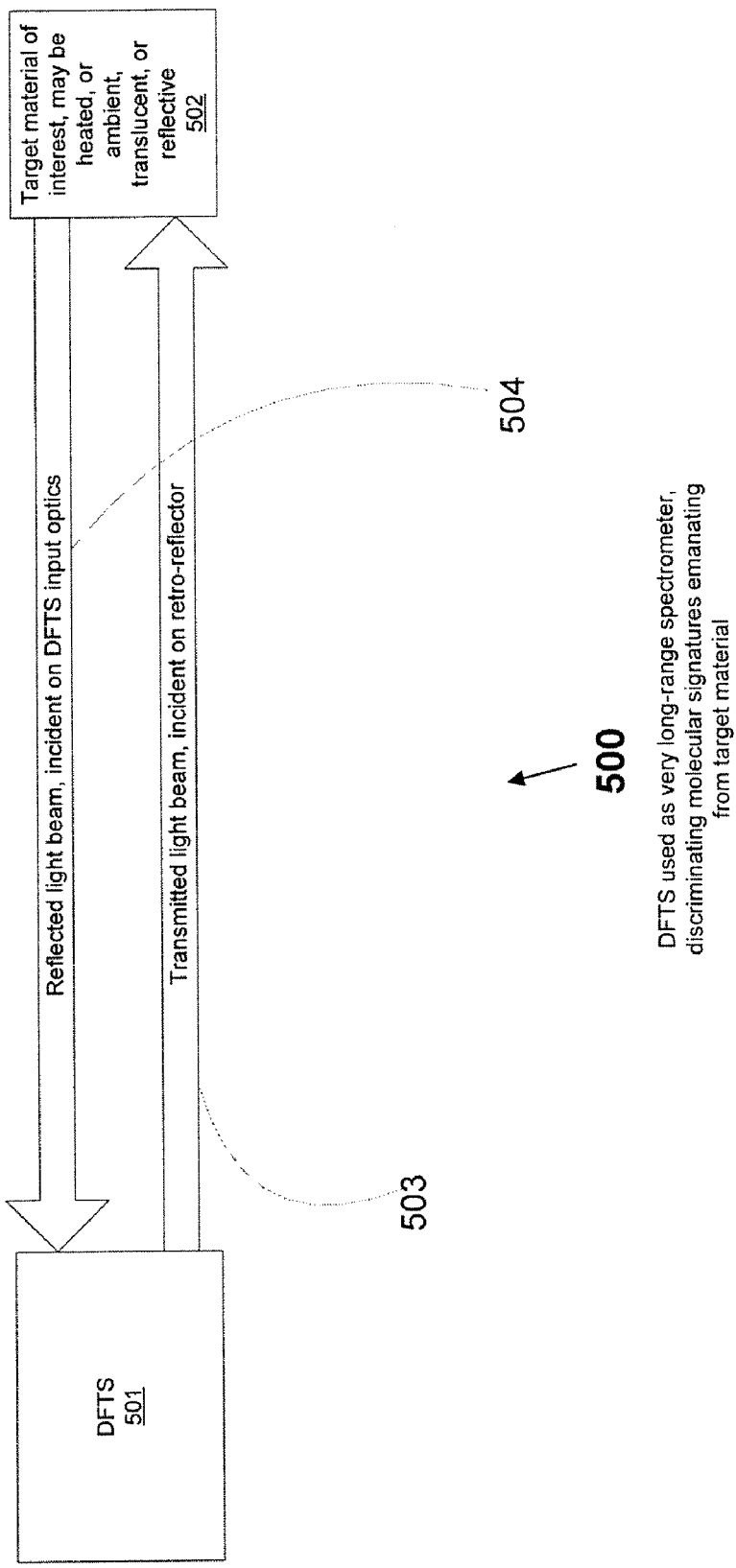
FIG. 5 depicts an example DFTS using a retro-reflector, which may or may not be modulated, for the measurement of distance between the DFTS Sensor and the retro-reflector.

The Sensor may be used to remotely identify the presence of e-coli, toxins, or biological taggants, including, but not limited to chemical, biological, radiological, nuclear, or environmental ("CBRNE") identifiers. This may be done to discriminate e-coli in foodstuffs in either a factory and/or packaging setting, or in the growing fields. In the packaging facility, the illuminating laser beam may pass over, or through the plastic food wrap. The Sensor will be tuned to those spectral bands which are characteristic of the molecules of interest. The Sensor will have a stored library of spectral bands which correspond to the target molecules. When the target signatures correlate to the library signatures, the presence of e-coli, or another appropriate toxin, will be indicated. In the growing field configuration, the toxic effluents may be sensed by illuminating the growing region from a point near the field, with the Sensor on one side, and a retro-reflector on the other. In that configuration, the Sensor will sense the region of the atmosphere immediately above the growing crop, and will sense toxic emanations from the crop which rise into the atmosphere. The stimulated response, or the retro-reflection from the toxic effluent, will provide a tell-tale response at spectral bands relative to the particular toxic effluent sought for detection. This class of application is shown in FIG. 5, which shows a system 500 having a DFTS 501 used as a very long-range spectrometer, discriminating molecular signatures emanating from the target material 502. The target material 502 may be heated, or ambient, translucent or reflective. FIG. 5 also illustrates the transmitted light beams 503 from the DFTS 501 and the reflected light beams 504 from the target 502.

The Sensor may be used to remotely identify the presence of airborne anthropomorphic aspirations and emanations, including aspirations in vivo for medical diagnostics. Human being exhalations, or other emissions from the human body, are examined by the Sensor to ascertain the presence or absence of tell-tale emissions indicative of certain diseases. This class of application is shown in FIG. 5.

The Sensor may be used to remotely identify the presence of emissions existing at long range and to approximate the geo-position of such emissions existing in remote or denied locations. In one example of this embodiment, the Sensor will detect $CO_2$ from mines or caves to find trapped miners or fugitives. Such capability could be used to sense lost mountain climbers, miners in collapsed mines, or lost persons in a forest by discriminating $CO_2$, or other anthropomorphic emissions present in human sweat, urine, or moist areas of the human body. In another example of this embodiment, the Sensor 300 will detect adipocere emanations resulting from the decay of human remains, thereby allowing the identification of corpse locations in broad-area search scenarios. This class of application is shown in FIG. 5.

The Sensor may be used to augment security in high-traffic or high-value facilities. The Sensor can be tuned to various CBRNE-like substances to monitor a facility. In this mode, non-visible wavelength illuminators will be employed to sense the air directly above facility occupants or visitors to sense hazardous CBRNE emanations. Alternatively, the Sensor could be employed to examine air in heating, ventilation, or air-conditioning systems attached to high-traffic or high-value facilities to sense the presence of hazardous emissions. This class of application is shown in FIG. 5.

The Sensor may be used to diagnose illnesses using retro-reflections from human retinal scans. Spectral signatures from the human macula will provide indications of over eight hundred diseases. This class of application is shown in FIG. 5.

The Sensor may be used to remotely identify the presence and quantity of pollutants, including, but not limited to, mercury, sulfur dioxide, and other stack emissions from coal-fired power plants, and other manufacturing facilities that are currently monitored, or may be monitored in the future as new environmental concerns are identified and regulated. This class of application is shown in FIG. 5.

Examples for the embodiment using measurement of relative range and motion, including vibration, are presented next.

Figure 6:
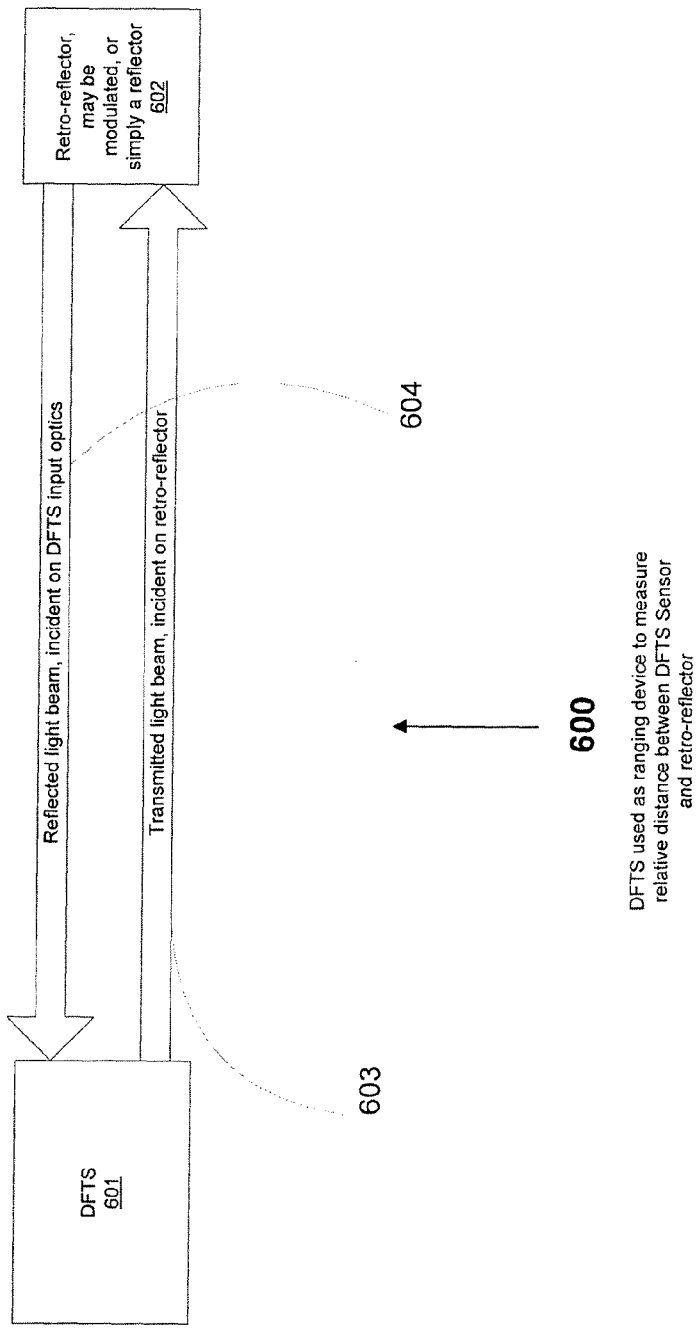
FIG. 6 depicts an example Sensor configuration using retro-reflection from one or more retro-reflectors to discriminate molecular signatures emanating from a target material which may be located at the site of the retro-reflector, on along the photon path between the DFTS Sensor and the retro-reflector.

The Sensor is capable of discriminating sub-nanometer motions of a target. The Sensor also has the ability to respond in real-time to such motions and vibrations. By comparing fringe shifts at different spectral bands, these measurements can be made with great precision. This class of applications is depicted in FIG. 6. Here the Sensor 601 transmits light beams 603 and receives photons (via light beam 604) reflected from a retro-reflector embedded on the surface of a target or object of interest 602. The reflected photons provide the necessary information to determine the relative range between the DFTS 601 and the retro-reflector 602. By arranging several retro-reflectors in a known pattern on the target surface, the relative orientation, attitude, or pose of the target surface can be determined. By measuring changes in the relative range in real time, the state of vibration of the surface can be determined.

The Sensor may be used to determine the position and attitude of a target, relative to the Sensor. For example in a satellite-to-satellite, satellite-to-ground target, or satellite-to-aircraft embodiment, the Sensor may be installed on a satellite, and the position and attitude of the target satellite, aircraft, or ground target, can be determined by the Sensor with exquisite precision. Reflections from the target's surface, or the gross motions of the target itself, can be exploited by the Sensor for this purpose. Markings on the target may be designed, similar to bar-codes, to identify a specific target. Taggants in the paint on the target may be used to uniquely identify a target, or the composition of the surface material may be sufficiently unique to contribute to, or allow, identification of a target.

Figure 7:
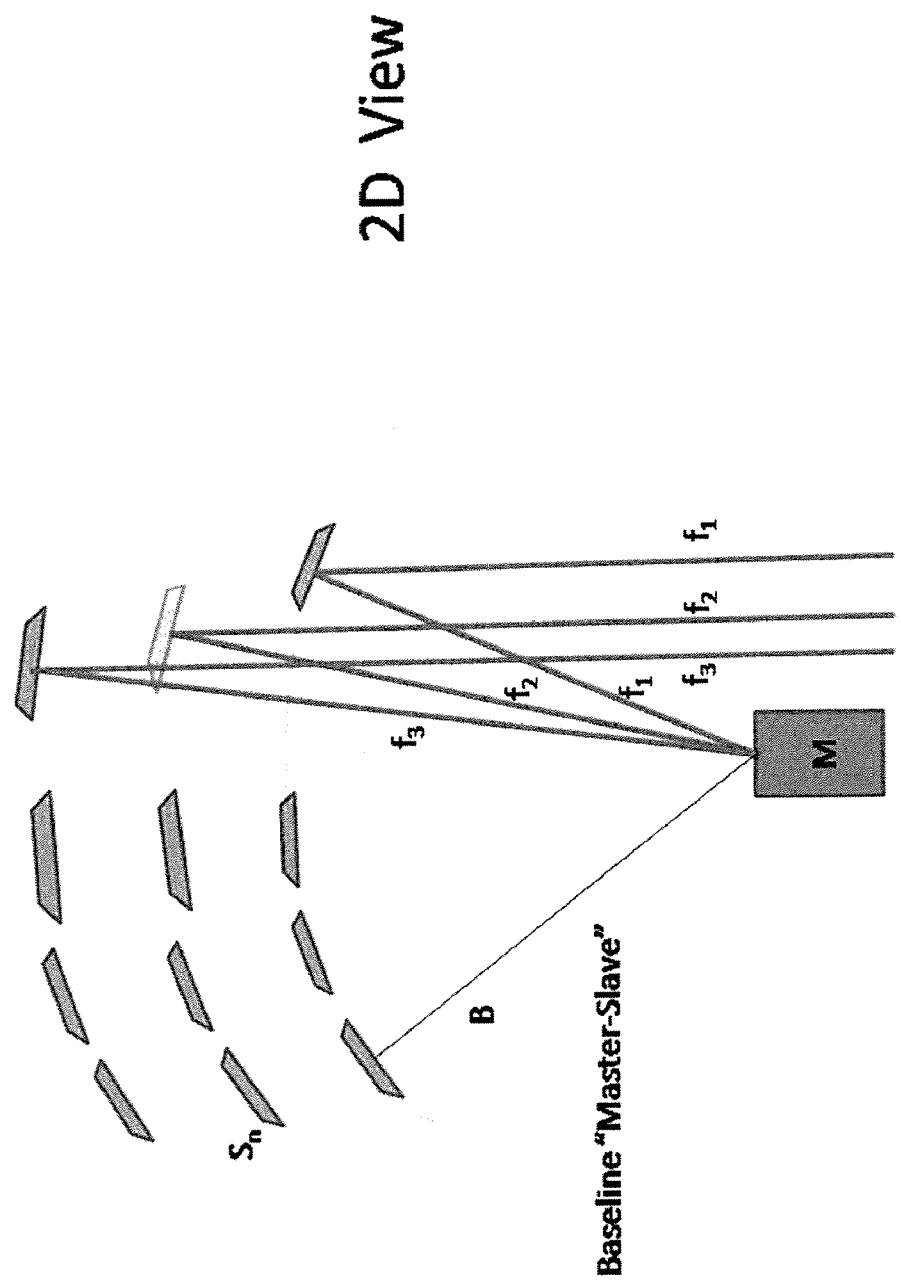
FIG. 7 depicts a two-dimensional satellite-to-satellite range and attitude measuring and control application, wherein the DFTS is mounted on the "Master" satellite, and the DFTS is used to measure the range to any number of "Slave satellites, which might comprise an array of reconfigurable optical or microwave reflectors in an adaptable array.

FIG. 7 depicts a typical two-dimensional satellite-to-satellite range and attitude measuring and control application, extending the generic case shown in FIG. 6, above. Retro-reflectors mounted on various locations of the Slave satellites, Sn, or reflective features on the Slave satellite surfaces, can provide the information necessary to determine the Slave satellites spatial orientation, or pose, with relation to the Master satellite, M, which carries the DFTS Sensor. In the configuration depicted in FIG. 7, the DFTS may be used to monitor the range, position, and attitude of an array of Slave satellites, Sn. Using this technique, spatially dispersed, virtual antennae may be reconfigured to accommodate transmission and reception at widely varying frequencies for microwave remote sensing, microwave remote sensing, telecommunications, or optical interferometry.

In FIG. 7, an example of a multi-frequency microwave transmission and reception array is depicted. Knowledge of the position of the Slave satellites, Sn, will allow the Master satellite, M, to automatically reconfigure the array, by directing changes in position, and pose, of the Slave satellites, Sn, and therefore optimize the array for transmission and reception at various frequencies, f1, f2, f3, etc. The array can, in essence, be re-tuned by positional reconfiguration, and the tuning can be optimized by foreknowledge and control of the precise position and attitude of each Slave satellite, Sn.

Figure 8:
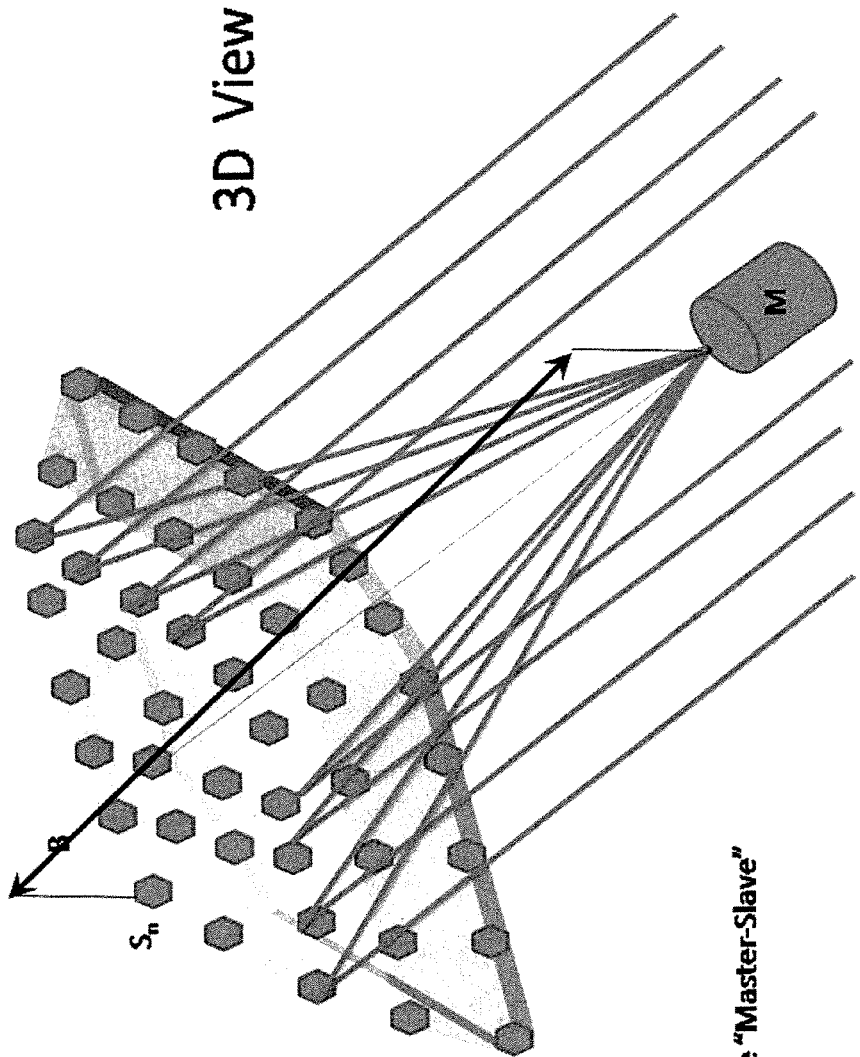
FIG. 8 depicts an example three-dimensional satellite-to-satellite range and attitude measuring and control application, similar to FIG. 7, above. Retro-reflectors mounted on various locations of the Slave satellites can provide the information necessary to determine the Slave satellites spatial orientation, or pose.
Figure 9:
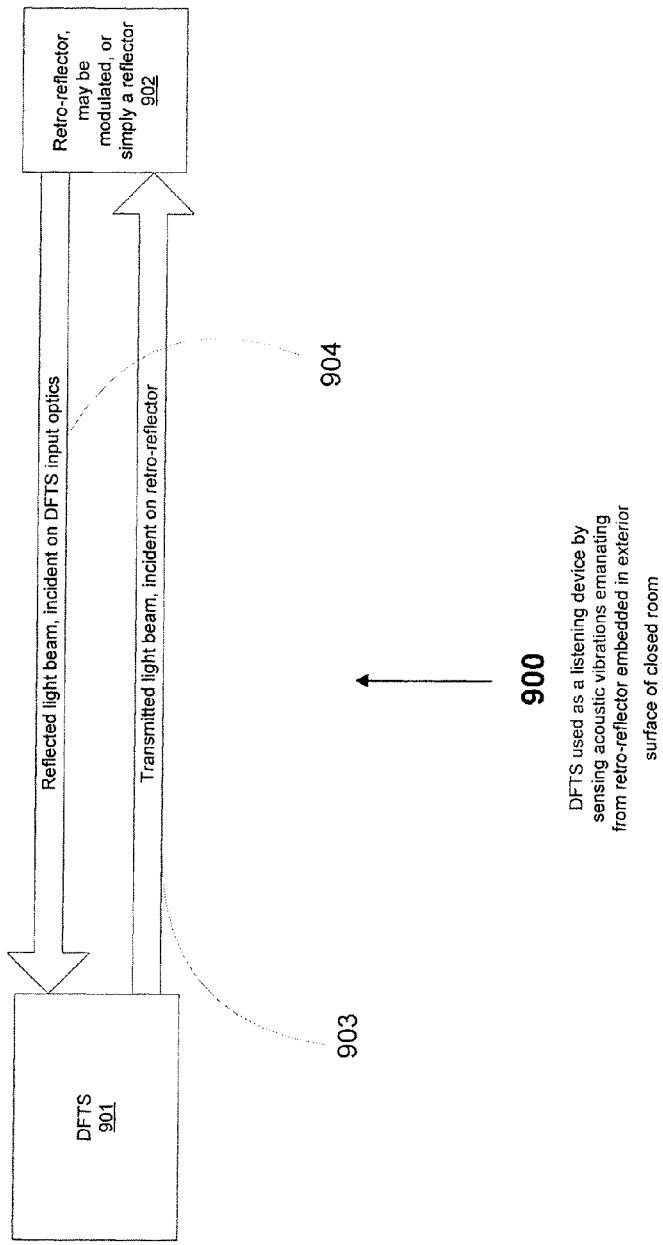
FIG. 9 depicts an example remote sensing application wherein the DFTS is used as a listening device, by sensing acoustic vibrations emanating from a retro-reflector embedded in the exterior surface (walls, ceiling, or floor) of a closed room or other denied space.

FIG. 8 depicts a three-dimensional perspective of a satellite-to-satellite range and attitude measuring and control application. Spatial separation between the components of the virtual antenna array is limited only by line-of-sight constraints. This creates the possibility for use of even very low frequency, very long wavelength remote sensing applications. Low frequency techniques demand long baseline, large aperture antennae. FIG. 8 is an extension and further description of a reconfigurable satellite array, showing Master satellite, M, with a three-dimensional array of Slave satellites, Sn, capable of operating at various frequencies simultaneously. This DFTS Sensor provides a means of establishing a precision baseline between Master satellite, M, and the Slave satellites, Sn, enabling the array to be used as a multi-wavelength interferometer. Such an array, functioning in either the optical or microwave domains, will provide very high resolution of objects at extremely long ranges.

The Sensor may be used to remotely eavesdrop on speakers at long-range by detecting the retro-reflections from the speaker's eyeballs at any line-of-sight range. Human voices modulate the skull, and the same vibrations which generate audible sound also modulate the eyeball(s) of the speaker. The Sensor can use dual wavelength illuminators, one to sense the frontal area of the eyeball, and the other to sense the rear macula region. Separately, or in combination, and by comparison of the resulting fringe shifts, the fringes will contain the voice signatures. In a related embodiment, the Sensor will remotely sense voice or infrasonics by measuring pressure fluctuations in front of the speaker. In this configuration, the audio in voiced speech modulates the air pressure directly in front of the speaker's face, the perturbations of which can be sensed by the Sensor. By sensing the retro-reflections from the speaker's eyeballs, the air path of the illuminating radiation will pass through this fluctuating pressure zone. This embodiment is susceptible to wind noise, but the use of standing gating, multiple wavelength illuminators, chopping, adaptive optics, or jitter techniques may be used to minimize the impact of wind noise.

Figure 10:
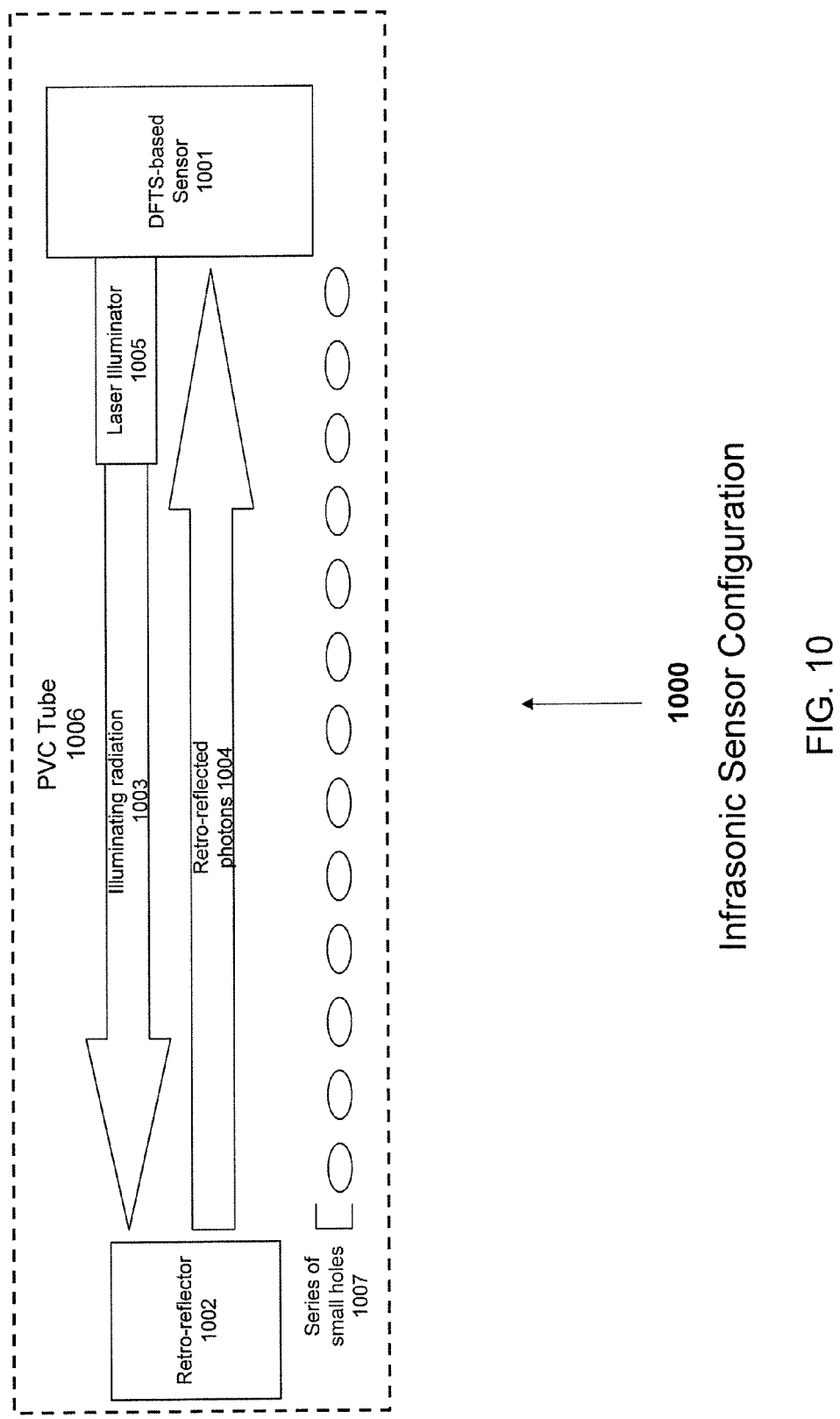
FIG. 10 depicts an example remote sensing application, wherein the DFTS is used as a very low frequency acoustic sensor, capable of measuring infrasonic fluctuations in the atmosphere at frequencies between 0.0001 Hertz and 15.0 Hertz by sensing the differential phase shift in a photon path between the DFTS Sensor and a retro-reflector at the end of a closed noise damping housing. The housing is shown with an array of openings to compensate for ambient wind and pressure effects.

The Sensor may be used to remotely sense infrasound (IF) for the detection of nuclear detonations and for detection of submarines. In this embodiment 1000, as depicted in FIG. 10, between the DTFS Sensor 1001 and the retro-reflector 1002 there is an approximately 30-meter long optical path for the travel of illuminating radiation 1003, and the reflection of retro-reflected photons 1004. This 30-meter long optical path is used as the air path over which the signal will be sampled. One or more laser illuminators 1005 will be used to sample the air path between the Sensor and the retro-reflector 1002. IF signals will modify the density of the atmosphere and generate fringe shifts which will be indicative of the presence of low-frequency IF waves. In some sites and circumstances, a longer air path may be warranted. In some situations, a closed tube, including, but not limited to a polyvinyl chloride type tube 1006, may be used to enclose the Sensor, retro-reflector 1002, and air path. In these cases, the tube will have a series of small holes 1007 in the bottom of the tube to couple to the IF signals, while at the same time minimizing the effects of wind noise. However, in most other embodiments, the polyvinyl tube is not required.

The Sensor may be used to remotely sense ocean-surface motions and vibrations and land motions and vibrations at sub-nanometer levels. Such ocean-surface motions may be indicative of the presence of a submarine, and the Sensor can, therefore, be used to detect the movement of the submarine. Additionally, the Sensor may be used to remotely sense the aerosols immediately above the ocean's surface, thus facilitating the discrimination of fish schools and submarines below the surface by exploitation of the aerosols. In one embodiment, the Sensor may be used not only to discriminate such nano-level motions; it will also discriminate and characterize the changing molecular makeup of the aerosols and surfactants of the surface. In such an embodiment, the Sensor can also discriminate oil and gas seeps at the ocean's surface to facilitate the search for resources, and it can discriminate tell-tale surface signatures indicative of the presence or motions of a passing submarine.

The Sensor will remotely sense voices and other acoustics using retro-reflected laser illumination, where the retro-reflector may be installed on a wall, ceiling, or floor of a denied room or area from which the sounds emanate. In this embodiment, the Sensor will mitigate hostage situations by providing audio information regarding events in the closed area. The illumination for this embodiment may comprise non-visible wavelength lasers, ambient sunlight, or self-generated illumination.

Figure 11:
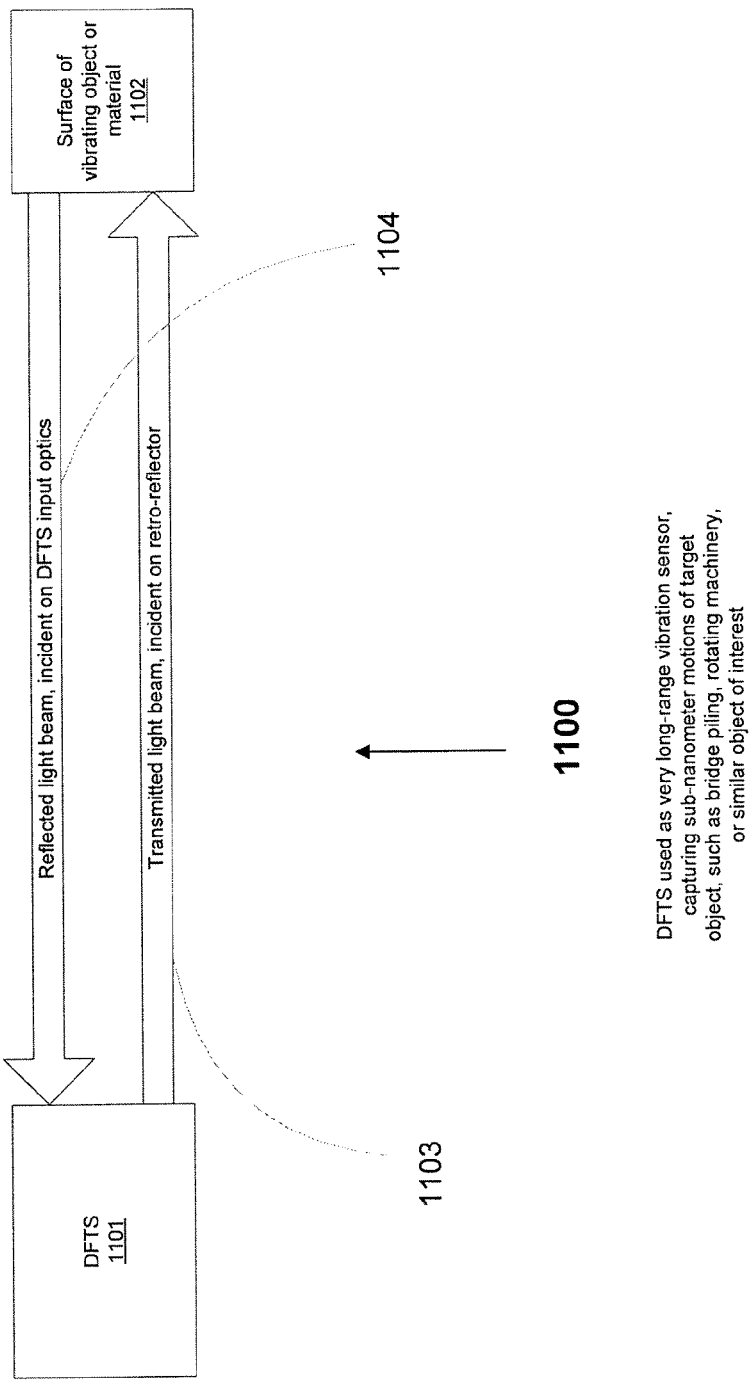
FIG. 11 depicts an example remote sensing application, wherein the DFTS is used as a very long-range vibration sensor, capturing sub-nanometer motions of a target object, such as a bridge piling, rotating machinery, or similar moving object of interest.
Figure 12:
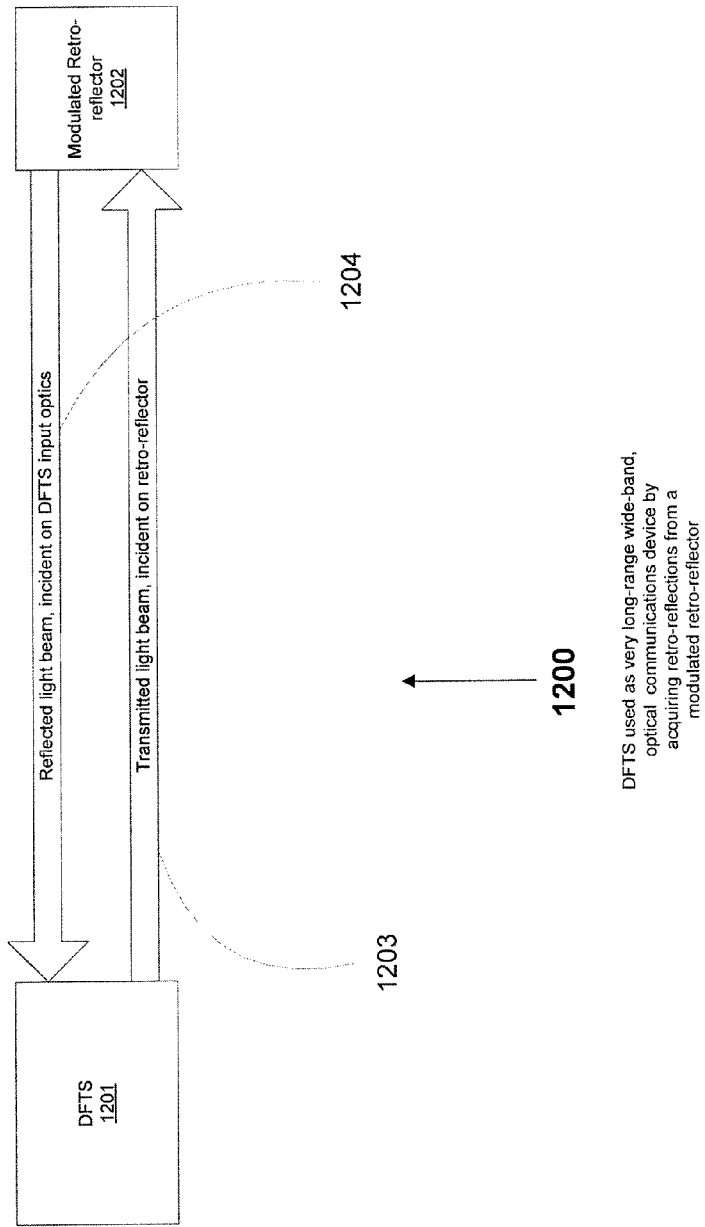
FIG. 12 depicts an example optical communications application, wherein the DFTS is used as a very long-range, wideband, optical communications device by acquiring retro-reflections from a modulated retro-reflector.

The Sensor will remotely sense vibrations and motion at audio and IF wavelengths from denied underground facilities, so as to sense the vibrations caused by underground centrifuges. Such remote sensing will take place in an airborne configuration. This class of application is shown in FIG. 11, which shows a system 1100 having a DFTS 1101 used as a very long-range vibration sensor, capturing sub-nanometer motions of a target object, such as a bridge piling, rotating machinery or similar object of interest 1102. FIG. 11 also illustrates the transmitted light beams 1103 from the DFTS 1101 and the reflected light beams 1104 from the object 1102.

The Sensor will remotely monitor building, structure, or bridge health by continuously measuring relative position, motions, and vibrations from a remote, fixed location. In this embodiment, the Sensor will sense retro-reflections from various points on a bridge, ascertain changes over time, and discern vibration patterns preliminary to and possibly indicative of impending structural failure. This class of application is shown in FIG. 11.

Obviously many other modifications and variations of the invention are possible in the light of the above teachings. It is therefore to be understood that the scope of the invention should be determined by referring to the following appended claims.

We claim:

1. A Sensor for spectrometric discrimination of a target's molecular composition, said Sensor comprising:
   a dispersed Fourier transform spectrometer;
   photon collecting optics;
   at least one fiber optic link coupled between the photon collecting optics and the dispersed Fourier transform spectrometer;
   at least one apparatus for signal conditioning and data acquisition coupled to an output of the dispersed Fourier transform spectrometer;
   at least one data processing device coupled to the at least one apparatus for signal conditioning and data acquisition;
   a plurality of reference interferogram data coupled to the at least one data processing device;
   at least one supporting software program implemented on the at least one data processing device; and
   at least one display coupled to the at least one data processing device, the Sensor using photon input from sunlight, incandescent light, or any broad spectrum source of light for spectrometric discrimination of the target's molecular composition.

2. The Sensor of claim 1, wherein said Sensor is optimized for the remote identification of the presence of toxins.

3. The Sensor of claim 1, wherein said Sensor is optimized for the remote identification of airborne anthropomorphic aspirations and emanations.

4. The Sensor of claim 1, wherein said Sensor is optimized for the monitoring of facility air.

5. The Sensor of claim 4, wherein the facility air is monitored through the heating, ventilation, or air-conditioning system.

6. The Sensor of claim 1, wherein said Sensor is optimized for the remote identification of the presence and quality of pollution emissions.

7. A Sensor comprising:
   a dispersed Fourier transform spectrometer;
   photon collecting optics;
   at least one fiber optic link coupled between the photon collecting optics and the dispersed Fourier transform spectrometer;
   at least one apparatus for signal conditioning and data acquisition coupled to an output of the dispersed Fourier transform spectrometer;
   at least one data processing device coupled to the at least one apparatus for signal conditioning and data acquisition;
   a plurality of reference interferogram data coupled to the at least one data processing device;

at least one supporting software program implemented on the at least one data processing device; and at least one display coupled to the at least one data processing device, wherein the Sensor discriminates sub-nanometer motions of a target.

8. The Sensor of claim 7, wherein the Sensor is optimized for the remote detection of the retro-reflections from a speaker's eyeball.

9. The Sensor of claim 7, wherein the Sensor is optimized for the remote detection of infrasound to enable the detection of nuclear detonations and submarines.

10. The Sensor of claim 7, wherein the Sensor is optimized for the remote detection of ocean-surface and land-surface motions and vibrations.

11. The Sensor of claim 1, wherein the Sensor is optimized for the remote detection of aerosols immediately above the ocean's surface.

12. The Sensor of claim 7, wherein the Sensor is optimized for the remote detection of voices and other acoustics using retro-reflected laser illumination.

13. The Sensor of claim 7, wherein the Sensor is optimized for the remote detection of vibrations and motion at audio and infrasound wavelengths.

14. The Sensor of claim 7, wherein the Sensor is optimized for the remote monitoring of structure positioning, motion, and vibrations.

15. The Sensor of claim 7, wherein the Sensor is optimized for the determination of relative satellite-to-satellite position and attitude.

16. The Sensor of claim 7, wherein the Sensor is optimized for determination of relative satellite-to-ground target position and attitude.

17. The Sensor of claim 7, wherein the Sensor is optimized for determination of relative satellite-to-aircraft position and attitude.

18. A Sensor comprising:

a dispersed Fourier transform spectrometer;

photon collecting optics;

at least one fiber optic link coupled between the photon collecting optics and the dispersed Fourier transform spectrometer;

at least one apparatus for signal conditioning and data acquisition coupled to an output of the dispersed Fourier transform spectrometer;

at least one data processing device coupled to the at least one apparatus for signal conditioning and data acquisition;

a plurality of reference interferogram data coupled to the at least one data processing device;

at least one supporting software program implemented on the at least one data processing device; and at least one display coupled to the at least one data processing device, wherein the Sensor discriminates sub-nanometer motions of a target and performs spectrometric discrimination of the target's molecular composition.

19. The Sensor of claim 18, wherein the Sensor is optimized for determination of relative satellite-to-aircraft position and attitude by discrimination of both motions and molecular spectra.

20. The Sensor of claim 18, wherein the Sensor is optimized for determination of relative satellite-to-satellite position and attitude by discrimination of both motions and molecular spectra.

21. The Sensor of claim 18, wherein the Sensor is optimized for determination of relative satellite-to-ground target position and attitude by discrimination of both motions and molecular spectra.

* * * * *